United States Patent [19]

Manis et al.

[11] 4,393,137
[45] Jul. 12, 1983

[54] CLONING PLASMID FOR STREPTOMYCES

[75] Inventors: Jack J. Manis, Portage; Sarah K. Highlander, Oshtemo Township, Kalamazoo County, both of Mich.

[73] Assignee: The Upjohn Company, Kalamazoo, Mich.

[21] Appl. No.: 276,425

[22] Filed: Jun. 22, 1981

[51] Int. Cl.³ .................. C12N 15/00; C12N 1/20; C12N 1/00; C12R 1/465
[52] U.S. Cl. ............................ 435/172; 435/253; 435/317; 435/886
[58] Field of Search ............... 435/172, 253, 317, 91

[56] References Cited
U.S. PATENT DOCUMENTS
4,273,875 6/1981 Manis ............................ 435/317

OTHER PUBLICATIONS
Science, 196, Apr., 1977, editorial.
Bibb, M. et al., Nature 284, 1980, 526-531.
Schottel, J. L. et al., J. Bacteriol., 146, (1981), 360-368.
Suarez, J. E. et al., Nature, 286, (1980), 527-529.
Thompson, C. J. et al., Nature, 286, (1980), 525-527.

Primary Examiner—Alvin E. Tanenholtz
Attorney, Agent, or Firm—Roman Saliwanchik

[57] ABSTRACT

Novel chemical compound plasmid pUC1061 obtained by deletion of ~2.0 kilobases of DNA from the *Streptomyces espinosus* plasmid pUC6. This plasmid is useful as a cloning vehicle in recombinant DNA work. For example, using DNA methodology, a desired gene, for example, the glucose isomerase gene, can be inserted into the plasmid and the resulting plasmid can then be transformed into a suitable host microbe which, upon culturing, produces the desired glucose isomerase.

5 Claims, 2 Drawing Figures

CLONING PLASMID FOR STREPTOMYCES

BACKGROUND OF THE INVENTION

The development of plasmid vectors useful for recombinant DNA genetics among microorganisms is well known. The editorial in Science, Vol. 196, April, 1977, gives a good summary of DNA research. This editorial is accompanied by a number of supporting papers in the same issue of Science.

Similar DNA work is currently being done on industrially important microorganisms of the genus Streptomyces. See Bibb, M., Schottel, J. L., and Cohen, S. N. 1980. A DNA cloning system for interspecies gene transfer in antibiotic-producing Streptomyces. Nature 284, 526–531; Schottel, J. L., Bibb, M., and Cohen, S. N. 1981. Cloning and expression in *Streptomyces lividans* of antibiotic resistance genes derived from *Escherichia coli*. J. Bacteriol., 146, 360–368; Suarez, J. E., and Chater, K. F. 1980. DNA cloning in Streptomyces: a bifunctional replicon comprising pBR322 inserted into a Streptomyces phage. Nature, 286, 527–529; and, Thompson, C. J., Ward, J. M., and Hopwood, D. A. 1980. DNA cloning in Streptomyces: resistance genes from antibiotic-producing species. Nature, 286, 525–527.

Plasmid puC6 can be isolated from *Streptomyces espinosus* biotype 23724a, NRRL 11439. U.S. Pat. No. 4,273,875 discloses and claims pUC6.

BRIEF SUMMARY OF THE INVENTION

An unexpectedly high copy number plasmid is constructed by deletion of ~2.0 kilobases (kb) of DNA from plasmid pUC6. This high copy plasmid, named pUC1061, advantageously also contains only a single XhoI site that can be used or adapted to be used for the cloning of DNA sequences from any organism.

Plasmid pUC1061 is constructed by the in vitro deletion of ~2.0 kb of DNA from plasmid pUC6. The construction comprises the deletion of the smaller pUC6 XhoI restriction endonuclease fragment. The pUC1061 XhoI site can accept XhoI and SalI digested DNA because XhoI and SalI endonucleases generate compatible single stranded ends on DNA fragments. Further, DNA sequences containing other restriction sites can be cloned into the pUC1061 XhoI site to generate new vectors suitable for cloning DNA sequences generated by other endonucleases. Finally, the single stranded ends of XhoI digested pUC1061 DNA can either be enzymatically removed or filled in to give linear, blunt ended, double stranded pUC1061 DNA. This form of pUC1061 DNA can be blunt end ligated to blunt ended DNA fragments from any source.

Further utility of pUC1061 derives from its other single restriction sites for endonucleases BglII and BclI. These sites may also be available for cloning of DNA fragments.

Unexpectedly, and advantageously, pUC1061 has an elevated copy number relative to that for pUC6. The copy number of pUC1061 is ~200–500 per streptomycete genome equivalent compared to a copy number of 20–30 for pUC6. This high copy number of pUC1061 allows the detection of very low levels of expression of cloned genes by taking advantage of a tremendous gene dosage effect.

Plasmid pUC6 is obtainable from the novel microorganism *Streptomyces espinosus* biotype 23724a, NRRL 11439. This plasmid can be obtained from NRRL 11439 by growing the culture on a suitable medium, harvesting the culture after a suitable time, fragmenting the mycelia, and then lysing the mycelia. From this lysate it is possible to isolate essentially pure pUC6. pUC6 is characterized by standard characterization tests which include its molecular weight, approximately 6.0 megadaltons, sensitivity to re-striction endonucleases, and presence at 20–40 copies per *S. espinosus* NRRL 11439 cell.

REFERENCE TO THE DRAWINGS

FIG. 1—This shows the construction scheme for making pUC1061 from pUC6.

FIG. 2—Restriction endonuclease cleavage map for pUC1061.

The map is constructed on the basis of plasmid pUC1061 having a molecular length of ca. 7.2 kilobases. The restriction endonuclease abbreviations are as follows: (1) BglII is an enzyme from *Bacillus globigii;* (2) BclI is an enzyme from *Bacillus caldolyticus;* (3) PvuII is an enzyme from *Proteus vulgaris;* and (4) XhoI is an enzyme from *Xanthomonas holicola.* pUC1061 can be used to create recombinant plasmids which can be introduced into host microbes by transformation. The process of creating recombinant plasmids is well known in the art. Such a process comprises cleaving the isolated vector plasmid at a specific site(s) by means of a restriction endonuclease, for example, BglII, XhoI, and the like. The plasmid, which is a circular DNA molecule, is thus converted into a linear DNA molecule by the enzyme which cuts the two DNA strands at a specific site. Other non-vector DNA is similarly cleaved with the same enzyme. Upon mixing the linear vector or portions thereof and non-vector DNA's, their single-stranded or blunt ends can pair with each other and in the presence of a second enzyme, known as a DNA ligase, can be covalently joined to form a single circle of DNA.

DETAILED DESCRIPTION OF THE INVENTION

The Microorganisms and Plasmid

Figure 1:
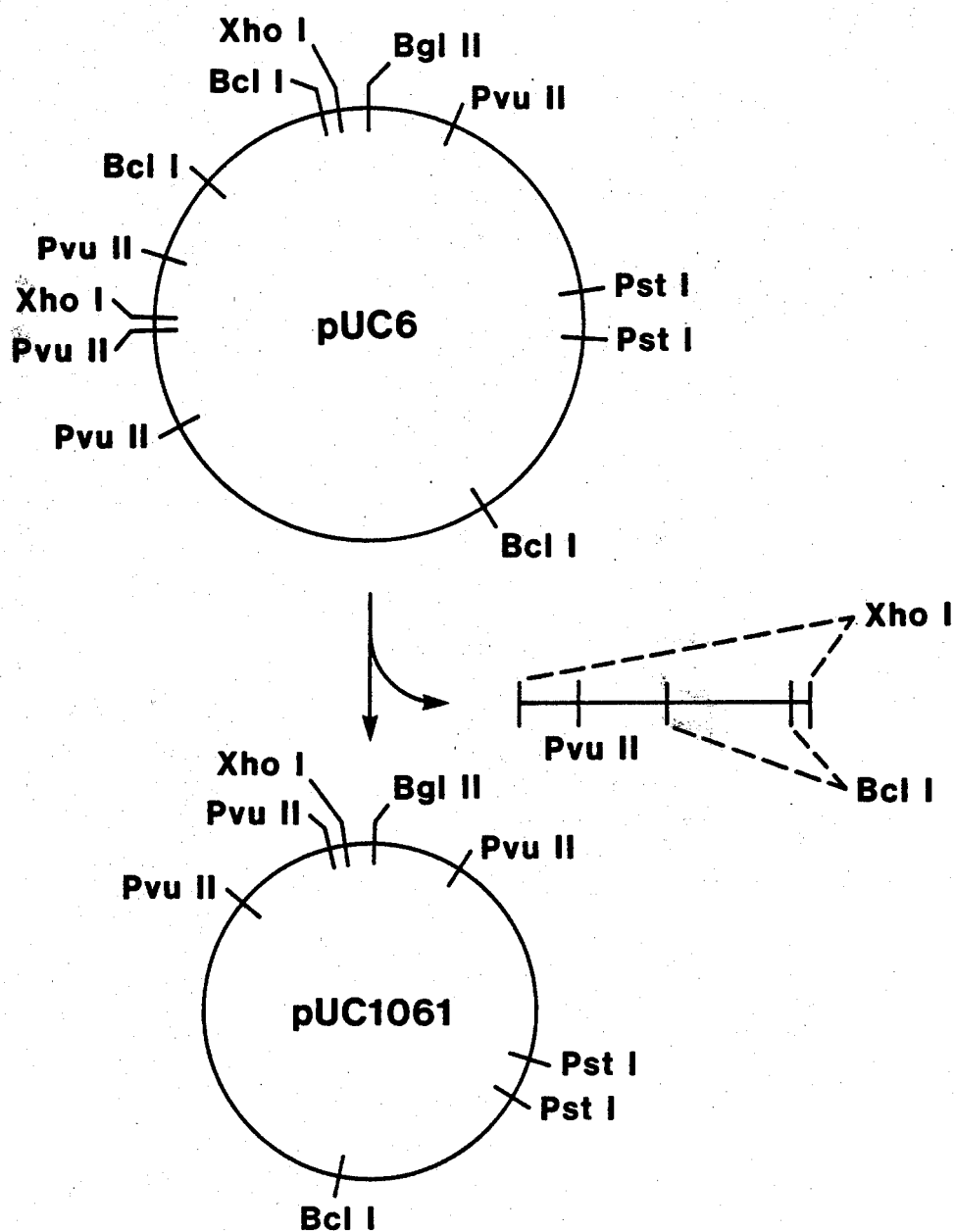

The following microorganisms are available from the permanent collection of the Northern Regional Research Laboratory, U.S. Department of Agriculture, Peoria, Ill., U.S.A.

NRRL 11439—*S. espinosus* biotype 23724a
NRRL 12488—*S. espinosus* biotype 23724a (pUC1061)

These deposits are available to the public upon the grant of a patent to the assignee, The Upjohn Company, disclosing them. The deposits are also available as required by foreign patent laws in countries wherein counterparts of the subject application, or its progeny, are filed. However, it should be understood that the availability of a deposit does not constitute a license to practice the subject invention in derogation of patent rights granted by governmental action.

| Restriction Endonuclease Sensitivities for Plasmid pUC6 and pUC1061 | | |
|---|---|---|
| | Number of Restriction Sites | |
| Endonuclease | pUC6 | pUC1061 |
| BglII | 1 | 1 |
| PvuII | 4 | 3 |
| BclI | 3 | 1 |
| XhoI | 2 | 1 |

-continued

Restriction Endonuclease Sensitivities
for Plasmid pUC6 and pUC1061

| Endonuclease | Number of Restriction Sites | |
| --- | --- | --- |
| | pUC6 | pUC1061 |
| PstI | 0(2)* | 0(2)* |
| SstI | 2 | 2 |
| BamHI | 0 | 0 |
| HindIII | 0 | 0 |
| KpnI | 0 | 0 |
| HpaI | 0 | 0 |
| EcoRI | 0 | 0 |
| XbaI | 0 | 0 |
| SalI | 6-7 | 5-6 |

*Plasmid pUC6 DNA isolated from *Streptomyces espinosus* biotype 23724a is not cleaved by PstI endonuclease. However, when pUC6 is cloned into *Escherichia coli* K-12 two PstI sites appear. Correspondingly, plasmid pUC1061 will have two PstI sites but they are masked in DNA isolated from *S. espinosus*.

Comparison of Copy Numbers per Host Genome Equivalent
for Plasmids pUC6 and pUC1061

| Plasmid | % Plasmid DNA[a] | Copy Number[b] |
| --- | --- | --- |
| pUC6 | 3.0 | 33 |
| pUC1061 | 45.0 | 473 |

[a]The percent plasmid DNA is determined by labeling DNA with [$^3$H—methyl]-thymidine and centrifuging a crude lysate of labeled cells in a dye-isopycnic density gradient. This resolves plasmid and chromosomal DNA's into two distinct bands. These density gradients are collected in 10 drop fractions which are measured for their radioactivity levels. The amount of radioactivity in the plasmid band relative to the total radioactivity in the gradient represents the percent of plasmid DNA present.
[b]We have used a molecular weight of $5.2 \times 10^9$ as being representative of the size of a *Streptomyces* chromosome in these copy number calculations.

The following examples are illustrative of the process and products of the subject invention but are not to be construed as limiting. All percentages are by weight and all solvent mixture proportions are by volume unless otherwise noted.

EXAMPLE 1

Isolation of Plasmid pUC6 from a Biologically Pure Culture of *Streptomyces espinosus*, biotype 23724a, NRRL 11439

The spores from a biologically pure culture of *Streptomyces espinosus* biotype 23724a, NRRL 11,439, are inoculated into 10 ml. of Difco Antibiotic Medium No. 3 Broth (Difco Labs., Detroit, Mich.): 0.15% Beef extract; 0.15% yeast extract; 0.5% peptone; 0.1% glucose; 0.35% NaCl; 0.368% $K_2HPO_4$; 0.132% $KH_2PO_4$.

The medium has previously been sterilized in a 50 ml. Erlenmeyer flask. After inoculation, the flask is incubated at 37° C. for about 36 to 48 hours on a Gump or New Brunswick rotary shaker operating at 100–250 rpm. Upon completion of the incubation, the mycelia-broth suspension in the flasks is homogenized under sterile conditions and is then mixed in a sterile 125 ml. Erlenmeyer flask containing 10 ml. of the above medium and also, advantageously 68% (w/v) sucrose and 1% (w/v) glycine. The addition of sucrose and glycine facilitates the subsequent lysing of the cells. The amounts of sucrose and glycine in the medium can be varied by routine adjustments with the goal being to facilitate the subsequent lysing of the cells. The flask is then incubated further for another 36 to 48 hours at 37° C. on a Gump rotary shaker, as above. After this incubation, the mycelia are separated from the broth by low speed centrifugation, for example, at 6000×g. for 15 minutes at 4° C. and decantation of the supernatant from the mycelial pellet.

The supernatant is discarded and the pellet is resuspended in 1.5 ml. of an isotonic buffer containing ethylenediaminotetraacetic acid (EDTA) and sucrose, e.g., TES buffer [0.03 M tris(hydroxymethyl)aminomethane (Tris), 0.005 M EDTA and 0.05 M NaCl; pH=8.0] containing 20% (w/v) sucrose. Next, 1.5 ml. of a 5 mg./ml. solution of lysozyme in the same buffer is added and the mixture is incubated at 37° C. for 30 minutes with occasional mixing. Then, 1.5 ml. of 0.25 M EDTA (pH=8.0) is added and this mixture is incubated 15 minutes at 37° C. Subsequently, the cell suspension is lysed by the addition of 2.5 ml. of a lytic mixture, e.g. [1.0% (w/v) Brij-58 (a detergent sold by Pierce Chem. Co., Rockford, Ill.), 0.4% (w/v) deoxycholic acid, 0.05 M Tris (pH=8.0) and 0.06 M EDTA] and incubation of this mixture at 37° C. for 20 minutes. The lysate is then sheared by passing it 5–10 times through a 10 ml. pipette. The sheared lysate is then digested with ribonuclease (140 μg/ml.) and pronase (300 μg/ml.) for an additional 20 minutes at 37° C. Alternatively, the cell-lysozyme-EDTA mixture can be digested with ribonuclease and pronase before lysis with a lytic agent such as 2% sodium dodecyl sulfate in water.

This crude lysate material is then mixed with a salt, for example, cesium chloride (preferred), and cesium sulfate, and the intercalating dye ethidium bromide to give a solution of density $\rho=1.550$. This solution is centrifuged to equilibrium at 145,000×g. (isopycnic density gradient centrifugation). The covalently closed circular plasmid DNA is then visible in the centrifuge tube under long wave ultraviolet (320 nm) illumination as a faint fluorescent band below the intensely fluorescent band of linear chromosomal and plasmid DNA's.

Covalently closed circular plasmid DNA is prepared for characterization by removing it from the isopycnic gradients, extracting the ethidium bromide by two treatments with one-third volume of isopropyl alcohol and then dialyzing the aqueous phase against an appropriate buffer, e.g., 0.1×SSC buffer (0.015 M NaCl, 0.0015 M sodium citrate; pH=7.4) to yield essentially pure pUC6.

EXAMPLE 2

Preparation of Plasmid pUC1061

Plasmid pUC6, prepared as described in Example 1, is linearized by digestion with restriction endonuclease XhoI as follows:

Approximately 0.5 μg of pUC6 DNA in 25 μl of TE buffer [0.01 M Tris.HCl, 0.01 M EDTA, pH 8.0] is mixed with an equal volume of 2X XhoI restriction enzyme buffer (0.3 M NaCl, 12 mM Tris.HCl [pH 7.4], 12 mM $MgCl_2$, 12 mM 2-mercaptoethanol) and two units of XhoI restriction enzyme. This sample is digested for one hour at 37° C.

The resulting digest is then applied to a 0.8% preparative low melting point agarose gel and electrophoresed for ~3 hours at 50 volts and 4° C. The resolved DNA fragments are visualized by ethidium bromide staining and long wave ultraviolet light illumination. The region of the gel containing the DNA is excised from gel and heated to 65° C. in the presence of 1.5 ml. of TE buffer to melt the gel and release the DNA from the gel matrix. This suspension is chilled and centrifuged at 37,000 xg to pellet the agarose. The supernatant is decanted and saved. The agarose pellet is extracted a second time by heating to 65° C. with TE buffer. The two supernatants are pooled and ethanol precipitated by the addition of 0.1 volume of Na Acetate and 2 volumes 95% ethanol at −20° C. The DNA precipitate is collected by centrifugation at 85,000 xg at 4° C. for 60 minutes. The precipitate is redissolved in 100 μl of TE buffer. The resulting largest fragment of pUC6 DNA precipitate is ligated as follows.

For ligation, 25 μl of DNA sample is mixed with 25 μl of 2X ligation buffer [132 mM Tris.HCl, 13.2 mM MgCl$_2$, 20 mM dithiothreitol (DTT), pH 7.6], 1 μl of 8 mM ATP and 1 unit of T4 DNA ligase. This mixture is incubated 1-2 hour at 22° C. and then used to transform Streptomyces espinosus protoplasts prepared from culture NRRL 11439.

Protoplasts are prepared from vegetative mycelia in the following manner. Spores are inoculated into S-medium [Okanishi, M., Suzuki, K. and Umezawa, H. 1974. Formation and reversion of streptomycete protoplasts: cultural condition and morphological study. J. Gen. Microbiol. 80, 389-400.] and grown 24-48 hrs at 37° C. This culture is homogenized and used to inoculate fresh S-medium cultures containing 0.5% glycine. The glycine supplemented cultures are grown another 24-48 hrs. at 37° C., harvested by centrifugation at B 3000 xg, washed once with 0.3 M sucrose and resuspended in 0.3 M sucrose. This suspension is sonicated 25-30 min. in a Branson model 220 ultrasonic water bath, pelleted at 3000 xg and the pellet is resuspended in P-medium [Okanishi, M., Suzuki, K. and Umezawa, H. 1974. Formation and reversion of streptomycete protoplasts: cultural condition and morphological study. J. Gen. Microbiol. 80, 389-400.] containing 5 mg/ml lysozyme. The mycelia and lysozyme are incubated at 37° C. until protoplasts are released. Mycelial debris are removed from the protoplast suspension by filtration through a sterile cotton plug. Residual lysozyme is removed by twice pelleting the protoplasts and washing them with P-medium. Finally, protoplasts are resuspended in P-medium.

Protoplast transformation is accomplished by mixing 0.5 ml of protoplast suspension with 0.05 ml of DNA sample and 0.5 ml of 20% polyethyleneglycol (PEG-6000) in P-medium and by allowing the mixture to stand 1 hr at room temperature. Next, 5 ml of P-medium is added and the protoplasts are pelleted. The pellet is taken up in a small volume (~e.g. 0.5 ml) and this mixture is plated on R$_2$ regeneration medium [Okanishi, M., Suzuki, K., and Umezawa, H., 1974. Formation and reversion of streptomycete protoplasts: cultural condition and morphological study. J. Gen. Microbiol. 80, 389-400] using 0.75% agar in R$_2$ medium as a soft agar overlay. After 7-10 days incubation at 37° C., transformants are detected by pock formation [Bibb, M. B., Ward, J. M., Hopwood, D. A. 1978. Transformation of plasmid DNA into Streptomyces at high frequency, Nature 274, 398-400].

The above procedure gives clones hosting pUC1061. These clones are designated S. espinosus (pUC1061), NRRL 12488.

Plasmid pUC1061 can be isolated from its S. espinosus host by well known procedures, e.g., using the crude lysate-isopycnic density gradient procedures described above. Once transformants containing pUC1061 are identified, they are separated as pure entities in a pure culture. This plasmid can be differentiated as a distinct entity by its unique restriction pattern.

Restriction endonucleases were obtained as commercial preparations from Miles Laboratories and New England Biolabs. Enzyme digestions were prepared in accordance with the conditions specified by the suppliers using at least a two-fold excess of endonuclease.

The digested samples were applied to 0.7-1% agarose gels and were electrophoresed for 3 hours at a constant applied voltage of 100 V. [Sharp, P. A., Sugden, J. and Sambrook, J. 1973. Detection of two restriction endonuclease activities in Haemophilus parainfluenzae using analytical agarose-ethidium bromide electrophoresis. Biochemistry 12, 3055-3063]. The molecular weights of restriction fragments were determined relative to the standard migration patterns of bacteriophage lambda DNA digested with enzyme HindIII [Murray, K. and Murray, N. E. 1975. Phage lambda receptor chromosomes for DNA fragments are made with restriction endonuclease III of Haemophilus influenzae and restriction endonuclease I of Escherichia coli. J. Mol. Biol. 98, 551-564] and by comparison to pUC6 DNA samples digested with the same endonucleases.

Examples of other hosts for the vector are other Streptomyces, E. coli K-12 derivatives [Bacteriological Reviews, Dec. 1972, pages 525-557] (these have been approved by the NIH Guidelines) and yeasts, other fungi, or other bacteria. It is recognized that these latter hosts would also hve to be approved by the NIH Guidelines.

The work described herein was all done in conformity with physical and biological containment requirements specified in the NIH Guidelines.

We claim:

1. *Streptomyces espinosus* (pUC1061) having the deposit accession number NRRL 12488.

Figure 2:
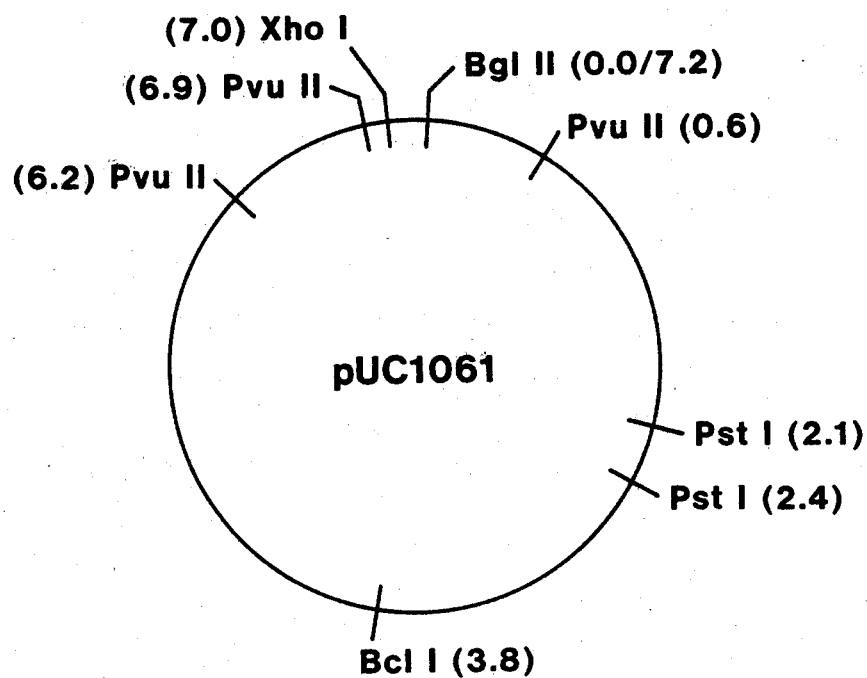

2. Plasmid pUC1061, characterized as shown by the restriction map in FIG. 2 of the drawings and having the following additional restriction sites: Sal I (5-6 sites) and Sst I (2 sites); lacking of restriction sites for the following restriction endonucleases: Bam HI, Hind III, Kpn I, Hpa I, EcoRI, and XbaI; and, having a molecular length of ca. 7.2 kilobases.

3. A process for preparing plasmid pUC1061 which comprises:
  (a) digestion pUC6 DNA with restriction endonuclease XhoI to obtain fragmented linear plasmid DNA; and,
  (b) ligating the largest fragment of said plasmid DNA to obtain plasmid pUC1061.

4. A process for cloning plasmid pUC1061 into a suitable host of the genus Streptomyces which comprises:
  (a) digestion of pUC6 DNA with restriction endonuclease XhoI to obtain fragmented linear plasmid DNA;
  (b) ligating the largest fragment of said plasmid DNA to obtain plasmid pUC1061; and,
  (c) transforming said plasmid into said suitable host.

5. A process, according to claim 4, wherein said Streptomyces is *S. espinosus* biotype 23724a.

* * * * *